United States Patent [19]

McCroskey

[11] Patent Number: 4,472,499

[45] Date of Patent: Sep. 18, 1984

[54] REAGENTS FOR THE DETERMINATION OF ENZYMES

[75] Inventor: Ralph P. McCroskey, Poway, Calif.

[73] Assignee: American Hoechst Corporation, Somerville, N.J.

[21] Appl. No.: 341,872

[22] Filed: Jan. 22, 1982

[51] Int. Cl.³ .................. C12Q 1/34; C12Q 1/00; C12Q 1/40; C12Q 1/42; C12N 9/96
[52] U.S. Cl. ........................................ 435/18; 435/4; 435/22; 435/21; 435/810; 435/188
[58] Field of Search ............... 435/4, 18, 21, 22, 23, 435/24, 805, 810, 188

[56] References Cited

U.S. PATENT DOCUMENTS

| | | | |
|---|---|---|---|
| 4,102,747 | 7/1978 | Duiscoll | 435/22 |
| 4,145,527 | 3/1979 | Burns et al. | 536/120 |
| 4,225,672 | 9/1980 | Hall | 435/22 |
| 4,233,403 | 11/1980 | Menson et al. | 435/22 |
| 4,243,753 | 1/1981 | Regnier et al. | 435/21 |

FOREIGN PATENT DOCUMENTS 2752501 5/1979 Fed. Rep. of Germany .
2755803 6/1979 Fed. Rep. of Germany .

OTHER PUBLICATIONS

Wilkinson, *The Principles and Practice of Diagnostic Enzymology*, Year Book Medical Publishers, Inc., Chicago, 143–144, (1976).
Good et al., Biochemistry, 5, (2), 467–477, (1966).

*Primary Examiner*—Esther M. Kepplinger
*Attorney, Agent, or Firm*—James R. Cartiglia; Natalie Jensen

[57] ABSTRACT

Assay reagents for the determination of enzymes such as α-amylase, α-glucosidase, β-glucosidase, and acid and alkaline phosphatases are described. The reagents comprise a substrate capable of releasing the chromophore p-nitrophenol at a rate proportional to the amount of enzyme being assayed and a buffer material that eliminates the temperature dependence of the chromophore.

7 Claims, No Drawings

REAGENTS FOR THE DETERMINATION OF ENZYMES

BACKGROUND OF THE INVENTION

The chromophore p-nitrophenol is extensively used in reagents designed to determine the presence and/or concentration of specific enzymes in test samples containing same. In spectrophotometric assays employing such reagents, the enzyme concentration is determined by the formula $$\text{enzyme units/liter} = \Delta A/\text{minute } X(1/\epsilon) \times F$$

where $\epsilon$ is the molar absorptivity of p-nitrophenol and F is a function of sample and reagent volumes and pathlength. The expression $(1/\epsilon) \times F$ is referred to as the calculation factor.

Within the pH range of 5 to 10 the molar absorptivity of p-nitrophenol varies with temperature and therefore the calculation factor varies with temperature. This variation necessitates (1) recalculation of the factor for each assay temperature employed; and (2) stringent maintenance of the selected temperature during assay.

Applicant overcomes the foregoing disadvantages by providing assay reagents wherein the temperature dependence of the chromophore is substantially eliminated.

SUMMARY OF THE INVENTION

The present invention relates to assay reagents for the determination of enzymes. More particularly, the present invention relates to assay reagents that employ the chromophore p-nitrophenol in combination with a buffer (or mixture of buffers) that substantially eliminates the temperature dependence of the chromophore. The consequence of rendering the chromophore temperature independent is enhanced test accuracy and the elimination of tedious calculations required when the molar absorptivity of the chromophore varies with temperature.

According to the present invention, there is provided a reagent for the determination of an enzyme in a sample containing same, which reagent comprises a substrate capable of releasing p-nitrophenol at a rate which is proportional to the amount of enzyme in the sample and a buffer having a $\Delta pK_a/°C$. of from about $-0.010$ to about $-0.031$ and a $pK_a$ in the range of 5 to 10 at 20° C., or mixtures of such buffers.

Preferred embodiments of the present invention relate to assay reagents for the determination of α-amylase, α-glucosidase, β-glucosidase, acid phosphatase or alkaline phosphatase.

DESCRIPTION OF THE INVENTION

When the chromophore p-nitrophenol is enzymatically released from a substrate containing a p-nitrophenyl group the following equilibrium occurs:

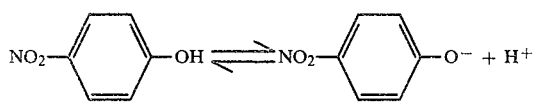

The rate of appearance of the p-nitrophenoxide species produces a corresponding rate of increase in absorbance at 405 nm which is proportional to the enzyme activity. As temperature changes, the equilibrium shifts and the measured absorbance increases or decreases even though the total amount of p-nitrophenol released by the substrate does not change. This change in measured absorbance, which is due to the change in temperature, produces a change in the molar absorptivity of p-nitrophenol. By employing a buffer(s) having (1) buffering capacity in the pH range of 5 to 10 and (2) a temperature dependent $pK_a$ which compensates for changes in molar absorptivity, one is able to eliminate or reduce the temperature dependence of p-nitrophenol in assay reagents containing same. This results in enhanced test accuracy and eliminates recalculation of the calculation factor (i.e. $1/\epsilon \times F$) for each assay temperature.

Substrates employed in the assay reagents of the present invention are those capable of enzymatically releasing p-nitrophenol. Such substrates include p-nitrophenyl derivatives of mono and oligosaccharides. In the case of oligosaccharides, the p-nitrophenyl radical is attached to the terminal glucose unit. Such substrates are described in U.S. Pat. Nos. 4,102,747, 4,233,403, 4,145,527, 4,225,672 and 4,147,860.

The substrate(s) employed in a particular assay reagent according to the present invention will depend on the enzyme to be assayed. For example, substrates useful for the assay of α-amylase are those selected from the group represented by the formula

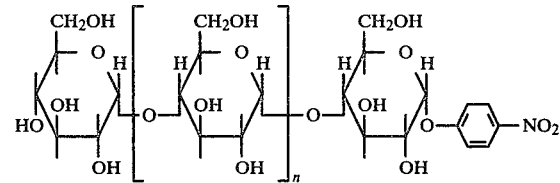

where n is 0 to 5, and mixtures of such substrates.

Particularly preferred substrates for the assay of α-amylase include p-nitrophenyl-α-maltopentaoside (n=3) and p-nitrophenyl-α-maltohexaoside (n=4), and mixtures thereof. Preferred substrates for the assay of α-glucosidase include p-nitrophenyl-α-glucoside and p-nitrophenyl-α-maltoside and mixtures thereof. Preferred substrates for the assay of β-glucosidase include p-nitrophenyl-β-glucoside and p-nitrophenyl-β-maltoside and mixtures thereof. A preferred substrate for the assay of alkaline and acid phosphatases is p-nitrophenyl-phosphate.

Buffers which are utilized with the above described substrates in the assay reagents of the present invention have a $\Delta pK_a/°C$. of from about $-0.010$ to about $-0.031$ and a $pK_a$ in the range of 5 to 10 at 20° C. Such buffers include, for example:

| | |
|---|---|
| MES | 2-(N—morpholino)ethanesulfonic acid |
| ADA | N—(2-acetamido)aminodiacetic acid |
| BIS-TRIS PROPANE | 1,3-bis(tris(hydroxymethyl)methylamino)propane |
| ACES | N—(2-acetamido)-2-aminoethane-sulphonic acid |
| MOPS | 3-(N—morpholino)propanesulfonic acid |
| TES | N—tris(hydroxymethyl)methyl-2-aminoethanesulfonic acid |
| HEPES | N—2-hydroxyethylpiperazine-N'—2-ethanesulfonic acid |
| HEPPS | N—2-hydroxyethylpiperazine-N'— |

| | |
|---|---|
| TRICINE | 3-propanesulfonic acid N—tris(hydroxymethyl)methylglycine |
| TRIS | tris(hydroxymethyl)aminomethane |
| BICINE | N,N—bis(2-hydroxyethyl)glycine |
| GLYCYLGLYCINE | |
| CHES | cyclohexylaminoethanesulfonic acid | as well as mixtures of such buffers.

The pH of the buffer material used in a particular assay reagent is adjusted, if necessary, by the use of appropriate acids and bases. Such adjustment preferably results in a buffer having a pH within ±1 pH unit of the pH optimum of the enzyme being assayed.

The assay reagents of the present invention are formulated by combining (a) the selected substrate(s) for the enzyme to be assayed; (b) any needed auxiliary enzymes and/or activators; and (c) a buffer having the requisite $pK_a$ and $\Delta pK_a/°C$. or a mixture of such buffers.

In the present invention, it is necessary that the amount of enzyme be rate limiting. Accordingly, individual components in the assay reagent should be present in amounts suitable to ensure that the observed reaction rate is characteristic of and determined by the rate of the reaction catalyzed by the enzyme being measured.

Enzyme activity is determined according to the present invention by dissolving the appropriate assay reagent in water to obtain a liquid reagent; mixing the liquid reagent with a sample containing the enzyme whereby the substrate contained in the reagent is hydrolyzed to yield p-nitrophenoxide; and measuring the rate of formation of p-nitrophenoxide.

The term "enzyme" as used herein refers to polypeptides which catalyze the hydrolysis of substrates capable of releasing p-nitrophenol.

DESCRIPTION OF SPECIFIC EMBODIMENTS

The following specific description is given to enable those skilled in the art to more clearly understand and practice the invention. It should not be considered as a limitation upon the scope of the invention but merely as being illustrative and representative thereof.

EXAMPLE I

The following buffers are prepared as indicated:

TRIS (0.05M)—a solution of 3.025 g of TRIS in 400 mL of distilled water is titrated with 12N hydrochloric acid to a pH of 8.97 at 22° C. and then diluted to 500 mL.

TRIS (0.1M)—a solution of 6.050 g of TRIS in 400 mL of distilled water is titrated with 12N hydrochloric acid to a pH of 8.97 at 22° C. and then diluted to 500 mL.

TRIS (0.5M)—a solution of 30.250 g of TRIS in 400 mL distilled water is titrated with 12N hydrochloric acid to a pH of 9.01 at 22° C. and then diluted to 500 mL.

HEPES (0.05M)—a solution of 1.19 g of HEPES in 100 mL of distilled water is titrated with a solution of HEPES, sodium salt (1.30 g/100 mL) to a pH of 6.90 at 22° C.

GLYCYLGLYCINE (0.02M)—a solution of 2.642 g of glycylglycine in 200 mL of distilled water is titrated with 1N sodium hydroxide to a pH of 8.31 at 22° C. and then diluted to 1 liter.

GLYCYLGLYCINE (0.20M)—a solution of 6.6 g of glycylglycine in 200 mL of distilled water is titrated with 1N sodium hydroxide to a pH of 8.34 at 22° C. and then diluted to 250 mL.

PHOSPHATE (0.10M)—a solution of 1.742 g of $K_2HPO_4$ in 100 mL of distilled water is titrated with a solution of $KH_2PO_4$ (1.361 g/100 mL) to a pH of 7.42 at 22° C.

TABLE 1 summarizes absorbance measurements ($A_{405}$) at different temperatures for four buffers containing p-nitrophenol. In the data tabulated, the concentration of ionized species (i.e. p-nitrophenoxide) is proportional to the absorbance of the solution at 405 nm in a 1 cm cuvette.

TABLE I

| | Buffer (Molarity) | pH at 22° C. | p-Nitrophenol (μmoles/mL) | $A_{405}$ | | |
|---|---|---|---|---|---|---|
| | | | | 22° C. | 30° C. | 37° C. |
| (1) | 0.05 M | 8.97 | 0.05 | 0.863 | 0.869 | 0.872 |
| (2) | 0.05 M | 6.90 | 0.10 | 0.808 | 0.813 | 0.814 |
| (3) | 0.02 M | 8.31 | 0.10 | 1.658 | 1.661 | 1.654 |
| (4) | 0.10 M | 7.42 | 0.10 | 0.505 | 0.530 | 0.571 |

(1) = TRIS;
(2) = HEPES;
(3) = GLYCYLGLYCINE;
(4) = PHOSPHATE

Based on absorbance measurements tabulated in TABLE 1, it is readily apparent that the p-nitrophenoxide concentration or absorbance in a buffer having negligible pH temperature dependence (i.e. phosphate buffer) increases approximately 13% between 22° C. and 37° C. In contrast, the p-nitrophenoxide concentration or absorbance in buffers having $\Delta pK_a/°C$. of −0.010 to −0.031 and a $pK_a$ in the range of 5 to 10 changes less than 1%.

TABLE 2 summarizes absorbance measurements ($A_{405}$) at different temperatures for various concentrations of two buffers containing p-nitrophenol. In the data tabulated, the concentration of ionized species (i.e. p-nitrophenoxide) is proportional to the absorbance of the solution at 405 nm in a 1 cm cuvette.

TABLE 2

| | Buffer (Molarity) | pH at 22° C. | p-Nitrophenol (μmoles/mL) | $A_{405}$ | | |
|---|---|---|---|---|---|---|
| | | | | 22° C. | 30° C. | 37° C. |
| (1) | 0.05 M | 8.97 | 0.05 | 0.863 | 0.869 | 0.872 |
| | 0.10 M | 8.97 | 0.05 | 0.879 | 0.884 | 0.887 |
| | 0.50 M | 9.01 | 0.05 | 0.871 | 0.876 | 0.879 |
| (3) | 0.02 M | 8.31 | 0.10 | 1.658 | 1.661 | 1.654 |
| | 0.20 M | 8.34 | 0.10 | 1.642 | 1.643 | 1.637 |

(1) = TRIS;
(3) = GLYCYLGLYCINE

Based on absorbance measurements tabulated in TABLE 2, it is readily apparent that the concentration or absorbance of p-nitrophenoxide is not affected by variations in buffer concentration when the buffer employed has a $\Delta pK_a/°C$. of −0.010 to −0.031 and a $pK_a$ in the range of 5 to 10.

EXAMPLE II

As α-amylase assay reagent having a pH of 6.90 at 22° C. is prepared by dissolving the following components in distilled water to provide the indicated concentration:

| | |
|---|---|
| p-Nitrophenyl-α-maltopentaoside | $8.5 \times 10^{-4}$ moles/L |
| p-Nitrophenyl-α-maltohexaoside | $6.5 \times 10^{-4}$ moles/L |
| Sodium chloride | $5.0 \times 10^{-2}$ moles/L |
| HEPES | $5.0 \times 10^{-2}$ moles/L |

| | |
|---|---|
| -continued | |
| α-Glucosidase | 3.3 × 10⁴ units/L |

Fifty μL of sample solution containing an unknown concentration of α-amylase is added to 2 mL of assay reagent at the selected assay temperature and the resulting assay solution is then incubated at the selected temperature. After 5 minutes the absorbance of the assay solution is measured at 405 nm in a 1 cm cuvette. Thereafter, absorbance measurements are made at one minute intervals and the measured absorbance change per minute (ΔA/minute) calculated.

The concentration of α-amylase in the sample is calculated by multiplying the absorbance change per minute (ΔA/minute) by a calculation factor (CF) which is derived from the formula $$CF = \frac{1}{\epsilon} \times F$$

where $\epsilon$ is molar absorptivity and F is a factor which is a function of sample and reagent volumes and pathlength. Measurement of the molar absorptivity of p-nitrophenol at three different assay temperatures yields the following values:

| Temperature | Molar Absorptivity (L × mole⁻¹ × cm⁻¹) |
|---|---|
| 22° C. | 8.08 × 10³ |
| 30° C. | 8.13 × 10³ |
| 37° C. | 8.14 × 10³ |

Calculation factors are derived for the assay at 22° C., 30° C., and 37° C. by multiplying the reciprocal of molar absorptivity (1/$\epsilon$) by a factor F which is derived from the expression $$F = \frac{\text{total assay volume (mL)} \times 10^6}{\text{sample volume (mL)} \times \text{pathlength (cm)}}$$

The values obtained for the calculation factors are as follows:

| Temperature | Calculation Factor |
|---|---|
| 22° C. | 5074 |
| 30° C. | 5043 |
| 37° C. | 5037 |

Based on the calculation factors tabulated above, it is readily apparent that the variance in the factors is negligible, i.e. the variance is only 0.7% between 22° C. and 37° C.

EXAMPLE III

An α-amylase assay reagent having a pH of 7.1 at 25° C. is prepared by dissolving the following components in distilled water to provide the indicated concentration:

| | |
|---|---|
| p-Nitrophenyl-α-maltoheptaoside | 5.0 × 10⁻³ moles/L |
| Sodium chloride | 5.0 × 10⁻² moles/L |
| Sodium phosphate | 5.0 × 10⁻² moles/L |
| α-Glucosidase | 3.0 × 10⁴ units/L |

Fifty μL of sample solution containing an unknown concentration of α-amylase is added to 2 mL of assay reagent at the selected assay temperature and the resulting assay solution is then incubated at the selected temperature. After 3 minutes the absorbance of the assay solution is measured at 405 nm in a 1 cm cuvette. Thereafter, absorbance measurements are made at one minute intervals and the measured absorbance change per minute (ΔA/minute) is calculated.

The concentration of α-amylase in the sample is calculated as described in EXAMPLE II using the formula $$\text{enzyme units/liter} = \Delta A/\text{minute} \times (1/\epsilon) \times F$$

where $\epsilon$ is molar absorptivity and F is a factor which is a function of sample and reagent volumes and pathlength.

Measurement of the molar absorptivity of p-nitrophenol at three different assay temperatures yields the following values:

| Temperature | Molar Absorptivity (L × mole⁻¹ × cm⁻¹) |
|---|---|
| 25° C. | 9.0 × 10³ |
| 30° C. | 9.5 × 10³ |
| 37° C. | 10.6 × 10³ |

Calculation factors are derived for the assay at 25° C., 30° C. and 37° C. by multiplying the reciprocal of molar absorptivity (1/$\epsilon$) by the factor F. The values for the calculation factors are as follows:

| Temperature | Calculation Factor |
|---|---|
| 25° C. | 13,667 |
| 30° C. | 12,947 |
| 37° C. | 11,604 |

Based on the calculation factors tabulated above, it is readily apparent that the variance in the factors is significant, i.e. the variance is 15.1% between 25° C. and 37° C.

What is claimed is:

1. A reagent for the temperature-independent determination of an enzyme in a sample containing same, comprising:
   a substrate capable of releasing p-nitrophenol at a rate proportional to the amount of enzyme in the sample, said substrate selected from the group consisting of p-nitrophenyl derivatives of mono and oligosaccharides and mixtures thereof; and
   a buffer which affects the release of p-nitrophenol from said substrate at a temperature-independent rate, said buffer selected from the group consisting of 2-(N-morpholino)ethanesulfonic acid, N-(2-acetamido)aminodiacetic acid, 1,3-bis(tris(hydroxymethyl)methylamino)propane, N-(2-acetamido)-2-aminoethanesulfonic acid, 3-(N-morpholino)propanesulfonic acid, N-tris(hydroxymethyl)methyl-2-aminoethanesulfonic acid, N-2-hydroxyethylpiperazine-N'-3-propanesulfonic acid, N-tris(hydroxymethyl)methylglycine,N,N-bis(2-hydroxyethyl)glycine, cyclohexylaminoethanesulfonic acid, and mixtures thereof.

2. A reagent according to claim 1 wherein said enzyme is α-amylase and said substrate is selected from the group represented by the formula

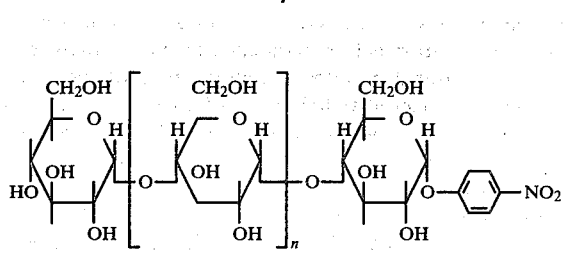

where n is 0 to 5, and mixtures of such substrates.

3. A reagent according to claim 2 further comprising a maltase.

4. A reagent according to claim 3 wherein the maltase is α-glucosidase.

5. A reagent according to claim 1 wherein the enzyme is α-glucosidase and the substrate is selected from the group represented by the formulas

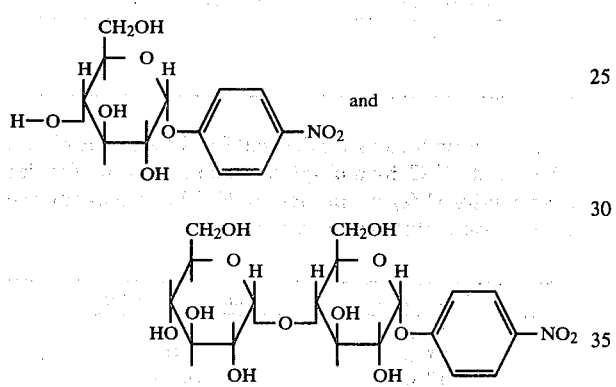

and mixtures thereof.

6. A reagent according to claim 1 wherein the enzyme is β-glucosidase and the substrate is selected from the group represented by the formulas

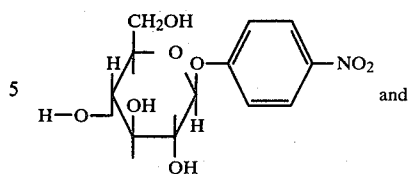

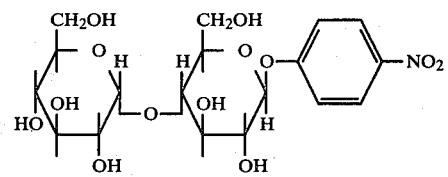

and mixtures thereof.

7. A process for determining an enzyme in a sample containing same, comprising:
(1) adding to said sample, a reagent comprising:
a substrate capable of releasing p-nitrophenol at a rate proportional to the amount of enzyme in the sample, said substrate selected from the group consisting of p-nitrophenyl derivatives of mono and oligosaccharides and mixtures thereof; and
a buffer which affects the release of p-nitrophenol from said substrate at a temperature-independent rate, said buffer selected from the group consisting of 2-(N-morpholino)ethane-sulfonic acid, N-(2-acetamido)aminodiacetic acid, 1,3-bis(tris(-hydroxymethyl)methylamino)propane,N-(2-acetamido)-2-aminoethanesulfonic acid, 3-(N-morpholino)propanesulfonic acid, N-tris(hydroxy-methyl)methyl-2-aminoethanesulfonic acid, N-2-hydroxyethylpiperazine-N'-3-propane-sulfonic acid, N-tris(hydroxymethyl)methyl-glycine,N,N-bis(2-hydroxyethyl) glycine, cyclohexylaminoethane-sulfonic acid, and mixtures thereof and
(2) determining the enzyme activity by the release of p-nitrophenol.

* * * * *

REEXAMINATION CERTIFICATE (944th)
United States Patent [19]

McCroskey

[11] B1 4,472,499
[45] Certificate Issued  Nov. 8, 1988

[54] REAGENTS FOR THE DETERMINATION OF ENZYMES

[75] Inventor: Ralph P. McCroskey, Poway, Calif.

[73] Assignee: American Hoechst Corporation, Somerville, N.J.

Reexamination Request:
No. 90/001,185, Mar. 2, 1987

Reexamination Certificate for:
Patent No.: 4,472,499
Issued: Sep. 18, 1984
Appl. No.: 341,872
Filed: Jan. 22, 1982

[51] Int. Cl.[4] .................... C12Q 1/34; C12Q 1/00; C12Q 1/40; C12Q 1/42; C12N 9/96
[52] U.S. Cl. ........................................ 435/18; 435/4; 435/22; 435/21; 435/810; 435/188
[58] Field of Search ............... 435/4, 18, 22, 21, 23, 435/24, 805, 810, 188

[56] References Cited
U.S. PATENT DOCUMENTS
4,102,747  7/1978  Driscoll et al. ............... 435/22

FOREIGN PATENT DOCUMENTS
2755803  6/1979  Fed. Rep. of Germany .

OTHER PUBLICATIONS

Good et al, Biochemistry, 5(2): 467–477, "Hydrogen Ion Buffers for Biological Research", (1966).
McCroskey et al, "Abstracts, J. Clinical Chemistry and Clinical Biochemistry", vol. 19, No. 8, Aug. 1981, p. 645.

*Primary Examiner*—Esther M. Kepplinger

[57] ABSTRACT

Assay reagents for the determination of enzymes such as α-amylase, α-glucosidase, β-glucosidase, and acid and alkaline phosphatases are described. The reagents comprise a substrate capable of releasing the chromophore p-nitrophenol at a rate proportional to the amount of enzyme being assayed and a buffer material that eliminates the temperature dependence of the chromophore.

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-7 are cancelled.

* * * * *